United States Patent [19]

Tsukada

[11] Patent Number: 5,211,632
[45] Date of Patent: May 18, 1993

[54] INFUSER WITH BALLOON FOR INFUSING MEDICINE
[75] Inventor: Osamu Tsukada, Nagano, Japan
[73] Assignee: Tsukada Medical Research Co., Ltd., Tokyo, Japan
[21] Appl. No.: 776,312
[22] PCT Filed: Feb. 28, 1990
[86] PCT No.: PCT/JP90/00266
§ 371 Date: Dec. 18, 1991
§ 102(e) Date: Dec. 18, 1991
[87] PCT Pub. No.: WO91/12835
PCT Pub. Date: Sep. 5, 1991
[51] Int. Cl.$^5$ ............................................. A61M 37/00
[52] U.S. Cl. .................................. 604/132; 604/246; 222/212
[58] Field of Search ............... 604/118, 131, 132, 141, 604/212, 213, 246, 247, 248; 128/DIG. 12; 222/209, 212, 386.5, 398

[56] References Cited

U.S. PATENT DOCUMENTS

| | | | |
|---|---|---|---|
| 3,469,578 | 9/1969 | Bierman | 604/246 |
| 4,318,400 | 3/1982 | Peery et al. | 604/174 |
| 4,909,790 | 3/1990 | Tsujikawa et al. | 604/132 |
| 4,998,918 | 3/1991 | Mimura | 604/132 |

FOREIGN PATENT DOCUMENTS

| | | |
|---|---|---|
| 0172586 | 2/1986 | European Pat. Off. . |
| 0295504 | 12/1988 | European Pat. Off. . |
| 102252 | 8/1981 | Japan . |
| 64-70069 | 3/1989 | Japan . |

Primary Examiner—John D. Yasko
Assistant Examiner—Anthony Gutowski
Attorney, Agent, or Firm—Wenderoth, Lind & Ponack

[57] ABSTRACT

An infuser for continuously infusing a solution of medicine includes a tubular main body having a flow path which extends along the longitudinal axis of the body. An inlet portion having a check valve, an injection port, or a one-way cock is connected to one end of the body. A cylinder with a closed bottom is slidably connected to the other end of the body. The bottom of the cylinder is directed outwardly. The cylinder or the other end of the body is provided with a plurality of holes. A change-over valve is provided in the flow path at an intermediate portion of the body. An outlet portion is connected to the change-over valve. A control portion for controlling the outflow of the solution of medicine is provided in the outlet portion. A balloon made from an elastic material surrounds the holes. One circumferential portion of the balloon is air-tightly secured to the outer periphery of the cylinder at a given position and another circumferential portion of the balloon is air-tightly secured to the outer periphery of the cylinder at a given position. In use, a given amount of the solution of medicine is infused into the balloon through the inlet portion. The solution of medicine in the balloon flows out continuously for a long time through the outlet control portion and an indwelling retainer attached to the outlet portion.

2 Claims, 6 Drawing Sheets

INFUSER WITH BALLOON FOR INFUSING MEDICINE

BACKGROUND OF THE INVENTION

1. Field of the Invention

The present invention relates to an infuser for continuously infusing predetermined volume of a solution of medicine into the human body within a predetermined period of time.

2. Description of the Related Art

There are two conventional methods of infusing a solution of medicine into the human body over a relatively long period of time: in one method, the solution of medicine is injected from an injecting needle or catheter, which is attached to a syringe containing the solution of medicine, by operating the syringe manually, electrically or by utilizing the action of a spring; and in the other method, an installation bottle containing the solution of medicine is used, and the solution is caused to drop therefrom under gravity or in an electrical manner.

In a case where the solution of medicine is infused into the human body over from a few minutes to a few hours, an injecting needle of a catheter must be kept attached to a syringe or instillation bottle serving as a medicine supplier, and this causes great inconvenience to the operator as well as to the patient.

For instance, in a case where an infusion is continuously carried out in a manual fashion, the movement of both the patient and the operator is restricted for a certain period of time, and this gives them great pains mentally and physically. It is generally believed that people can remain in the same posture only for 1 or 2 minutes under such a condition. In contrast, in a case where the infusion of the solution of medicine is carried out electrically or by utilizing the action of a spring, a power source must be secured near the infusion site, and a syringe must properly be placed. This also restricts the action of the patient.

In addition, when the solution of medicine is continuously infused into the human body by utilizing the instillation method, a comparatively large amount of a supplemental liquid relative to the medicine needs to be used, and even if the patient does not require such a supplemental liquid, he/she must be subjected to the infusion of the same. Moreover, an instillation bottle or container must be placed at a position higher than where the patient is lying, and a complicated and long conduit is required to connect the injecting needle or catheter to the instillation bottle. This also restricts the movement of the patient, and the operator is required to confirm whether or not the instillation of the solution of medicine is being carried out properly.

Japanese Patent Publication No. 45799/1980 discloses a flow control device for use in infusing a solution of medicine into the human body. In this device, a core having a spiral groove formed therein is inserted in a sleeve, and this sleeve is clamped by means of a ring so as to control the flow of the solution. However, with this flow control device, it is not possible to continuously infuse the solution of medicine over a long period of time.

U.S. Pat. No. 4,318,400 discloses an infuser for continuously infusing a solution of medicine. In this infuser, a balloon containing therein the solution of medicine is inserted in a cylinder, and the balloon contracts in the axial direction with the solution of medicine contained therein being injected therefrom by virtue of the contracting action of the balloon. However, this infuser is disadvantageous in that the solution contained in the balloon cannot completely be discharged therefrom.

In view of the above drawbacks, the present applicant has previously developed "An Infuser with a Balloon for Continuously Infusing a Solution of Medicine" (Japanese Patent No. 1384289) for infusion into the human body over a comparatively long period of time and which has a simple structure is easy to handle and is reliably safe.

This patented infuser comprises a tubular main body having a flow path that extends formed along the longitudinal axis of the tubular main body, a portion with a check valve provided at one end of the tubular main body to allow the solution of medicine to be infused therefrom into the tubular main body, a portion provided at the other end of the tubular main body to allow a solution of medicine to be injected therefrom, a member provided at an intermediate position along the length of the tubular main body to shut off the flow path, an inlet hole and an outlet hole (or outlet hole with a fine porous membrane) provided in the neighborhood of the shut off member on the medicine infused portion side and medicine injecting portion side, respectively, in such a manner as to extend through the wall of the tubular main body, and a balloon made from an elastic material and surrounding the inlet and outlet holes, the balloon being air-tightly secured to the outer periphery of the tubular main body at the perimeter thereof.

In addition, the present applicant has also previously disclosed "An Infuser with a Balloon for Continuously Infusing a Solution of Medicine into a Blood Vessel" (the official Gazette of Japanese Patent Public Disclosure No. 11465/1987) which comprises the above patented infuser and an intravascular retainer connected to the medicine injecting portion of the same infuser.

Moreover, the applicant of the present invention also previously disclosed "An Infusing Catheter for Continuously Infusing a Solution of Medicine into a Urinary Bladder" (the Official Gazette of Japanese Patent Public Disclosure No. 11464/1987) that is intended to be used when continuously infusing a solution of medicine into the human body over a comparatively long period of time and which has a simple structure, is easy to handle and is safe to use.

In this catheter, a conventional common catheter for a urinary bladder is employed, and a recess is formed in a part of the outer periphery of the catheter at the proximate end thereof. A balloon made from an elastic material is provided on the catheter so as to surround the recess, and the balloon is air-tightly secured to the outer periphery of the catheter at the perimeter thereof. A capillary tube is provided on the wall of the catheter along the longitudinal axis thereof. This capillary tube is open at the proximate end thereof so as to form an outlet port for a solution of medicine and is caused to communicate with the recess at the proximate end. A portion allowing the solution of medicine to be infused therefrom into the balloon is air-tightly secured to the balloon at the central portion thereof, and a central passageway is provided at the center of the portion allowing the medicine to be infused. A valve is provided on the central passageway at the inlet end thereof, and the passageway communicates with the recess at the outlet end thereof.

The above-described infuser or catheter is provided with a capillary hole or capillary tube for controlling the time during which the solution of medicine is allowed to flow out. It is, however, difficult to actually form such a capillary hole or capillary tube, and even if this is possible, they are readily clogged with foreign matters.

In view of the above drawbacks, the present applicant succeeded in contriving a method of forming a capillary tube for controlling the time during which the solution of medicine is allowed to flow out with ease and previously disclosed "An Infuser with a Balloon for Continuously Infusing a Solution of Medicine" having a structure in which the clogging of a capillary tube is prevented (PCT-JP-88-01055).

This infuser comprises a tubular main body having a flow path that is formed along the longitudinal axis of the tubular main body. This tubular main body is provided at one end thereof with a portion with a check valve allowing the solution of medicine to be infused therefrom into the tubular main body and at the other end thereof with a portion allowing the solution of medicine to be injected therefrom. A predetermined volume of a normal temperature or thermosetting pourable resin that exhibits no adhesiveness relative to a specific material fills the other end of the tubular main body, and a linear, spiral or wound capillary wire made from a specific material and having a predetermined diameter is embedded in the pourable resin. This capillary wire extends into the tubular main body at one end thereof, and the other end thereof is guided so as to extend through the medicine injecting portion to the outside of the tubular main body. Holes are formed in the tubular main body in such a manner as to extend through the wall thereof, and a balloon made from an elastic material is provided so as to surround the holes with a circumferential portion thereof being air-tightly fixed to the outer periphery of the tubular main body.

The capillary wire is drawn to the outside of the tubular main body so as to form a capillary hole through the pourable resin portion, and an indwelling retainer for the human body can be fitted to the medicine injecting portion.

This medicine infuser, however, has a drawback in that minute burrs are formed on the inner surface of the capillary hole after the capillary wire has been drawn out. Thus, it is difficult to form a hole which will function steadily.

The present applicant has also disclosed "An Infuser with a Balloon for Continuously Infusing a Solution of Medicine" in which the time during which the solution of medicine is allowed to flow out is able to be variously changed and which has a steady capillary hole through which the solution of medicine is allowed to flow out (PCT-JP-89-00515).

This infuser comprises a tubular main body having a flow path that extends along the longitudinal axis of the tubular main body. This tubular main body is provided at one end thereof with a portion with a check valve or one-way cock allowing the solution of medicine to be infused therefrom into the tubular main body and at the other end thereof with a portion allowing the solution of medicine to be injected therefrom. A control portion for controlling the outflow of the solution of medicine is also provided adjacent to the medicine infused portion at the other end of the tubular main body. A plurality of holes are formed in the tubular main body in such a manner as to extend through the wall thereof, and a balloon made from an elastic material is provided so as to surround the holes with a circumferential portion thereof being air-tightly fixed to the outer periphery of the tubular main body.

In the infuser with a balloon for continuously infusing a solution of medicine developed by the present applicant, however, a rate of expansion and contraction of the balloon is different between a center portion and both end portions thereof, since the circumferential end portions of the balloon are secured to the tubular main body. Consequently, the solution of medicine flows under a high pressure and flow rate at the beginning of ejection while the solution flows under a low pressure and flow rate at the end of the ejection.

SUMMARY OF THE INVENTION

An object of the present invention is to provide an infuser with a balloon for continuously infusing a solution of medicine and in which a flow rate of the solution can be kept constant.

An infuser with a balloon for continuously infusing a solution of medicine in accordance with the present invention comprises a tubular main body having a flow path which is formed along the longitudinal axis of the body. An inlet portion having a check valve, an injection port, or a one-way cock is connected to one end of the body. A cylinder with a bottom is slidably connected to the other end of the body. The bottom of the cylinder is directed outwardly. The cylinder or the other end of the body is provided with a plurality of holes. A change-over valve is provided in the flow path at an intermediate portion of the body. An outlet portion for the solution of medicine is connected to the change-over valve. A control portion for controlling the outflow of the solution of medicine is provided in the outlet portion. A balloon made from an elastic material surrounds the holes. One circumferential portion of the balloon is air-tightly secured to the outer periphery of said body at a given position and another circumferential portion of the balloon is air-tightly secured to the outer periphery of the cylinder at a given position.

Preferably, scale marks are formed longitudinally on the outer periphery of that portion of the body which supports the cylinder.

BEST MODE FOR CARRYING OUT THE INVENTION

Referring to FIGS. 1 to 5, a basic structure of the infuser for continuously infusing a solution of medicine according to the present invention will now be described. The medicine infuser according to the present invention comprises a tubular main body 1, a balloon 2, a cylinder 3, a change-over valve 4, an inlet portion 5, and an outlet portion 6.

In this tubular main body 1, a flow path 11 extends in the longitudinal direction of the tubular main body. The inlet portion 5 allowing the solution of medicine to be infused therefrom into the tubular main body is provided at one end (at the right-hand side as viewed in FIG. 1) of the tubular main body 1, the change-over valve 4 is provided at an intermediate portion of the body 1, and the cylinder 3 with its bottom directed outwardly is connected slidably to the other end (at the left-hand side as viewed in FIG. 1 at the tubular main body 1).

Although the inlet portion 5, the change-over valve 4, and the outlet portion 6 may be formed unitarily with the tubular main body 1, they may be made of separate parts, as shown in the drawings, for convenience in the manufacturing and handling thereof. The inlet portion 5 is provided with a conventional check valve, injection port, or one-way cock 51. The check valve, injection port, or one-way cock 51 allows the solution of medicine to flow in a direction indicated by arrow 511 but not in the opposite direction, or serves to open or close the flow path 11.

The change-over valve 4 serves to selectively place the inlet portion 5 and the cylinder 3 in communication, the cylinder 3 and the outlet portion 6 in communication, the inlet portion 5 and the outlet portion 6 in communication, or all three in communication. For example, the valve 4 may be a conventional three-way cock.

Figure 1:
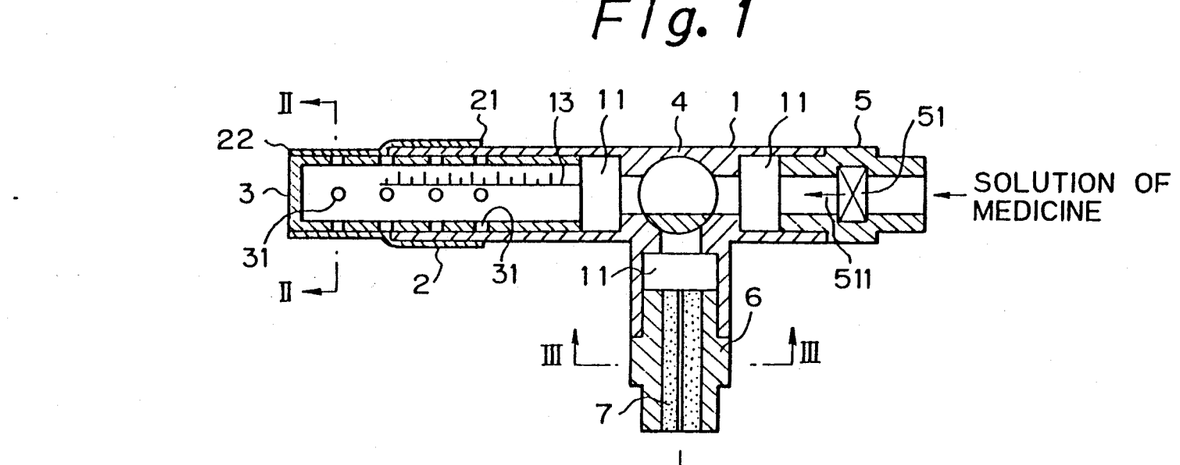
FIG. 1 is a longitudinal cross-sectional view of an infuser for continuously infusing a solution of medicine according to the present invention.
Figure 2:
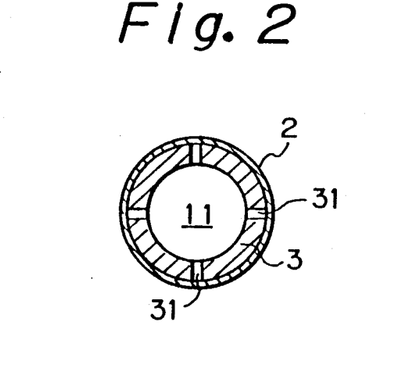
FIG. 2 is a transverse cross-sectional view taken along line II—II of FIG. 1.
Figure 3:
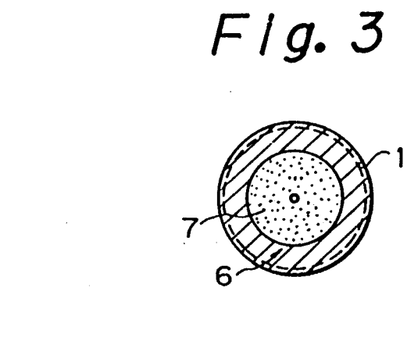
FIG. 3 is a transverse cross-sectional view taken along line III—III of FIG. 1.
Figure 5:
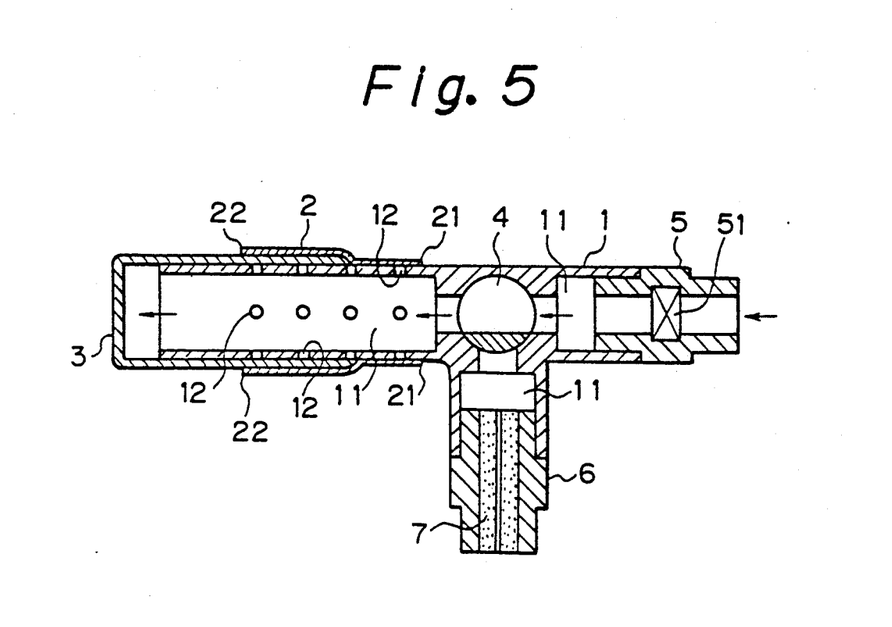
FIG. 5 is a longitudinal cross-sectional view of another embodiment of the infuser according to the present invention.

The cylinder 3 may be slidably mounted on the interior or the exterior of the tubular main body 1 as shown in FIG. 1 or 5. When the cylinder 3 is mounted on the interior, the cylinder is provided with a plurality of holes 31. When the cylinder is mounted on the exterior, the tubular main body is provided with a plurality of holes 12 (FIG. 5).

These holes 31 or 12 communicate with the flow path 11 of the main body 1.

Scale marks 13 are formed longitudinally on the outer periphery of the main body 1. The scale marks 13 indicate an amount of movement of the cylinder 3, and thus a user can know an amount of inflow or outflow of the solution of medicine.

The balloon 2 is attached to the tubular main body 1 and the cylinder 3 so that the balloon 2 surrounds the connection portions of the same. As shown in FIG. 1 or 5, one circumferential portion 21 of the balloon 2 is air-tightly secured to the outer periphery of the body 1 at a given position and the other circumferential portion 22 of the balloon 2 is air-tightly secured to the outer periphery of the cylinder 3 at a given position, so that the balloon 2 covers the open end of the tubular main body 1 or the open end of the cylinder 3 and the holes 31 or 12.

With the structure described above, the solution of medicine which leaks from the connected portions of the tubular main body 1 and the cylinder 3 or the holes is enclosed in the balloon 2 and cannot flow out of the infuser.

It is desirable that this balloon 2 be made from a material having good contraction and expansion properties, as well as good resistance to wear and toughness so that it is not easily damaged when a force is applied thereto from the outside. In particular, such a material is desirably transparent or translucent. Commercially available silicon rubber, latex rubber and so forth can be used as an optimal material for the balloon.

Figures 4A, 4B:
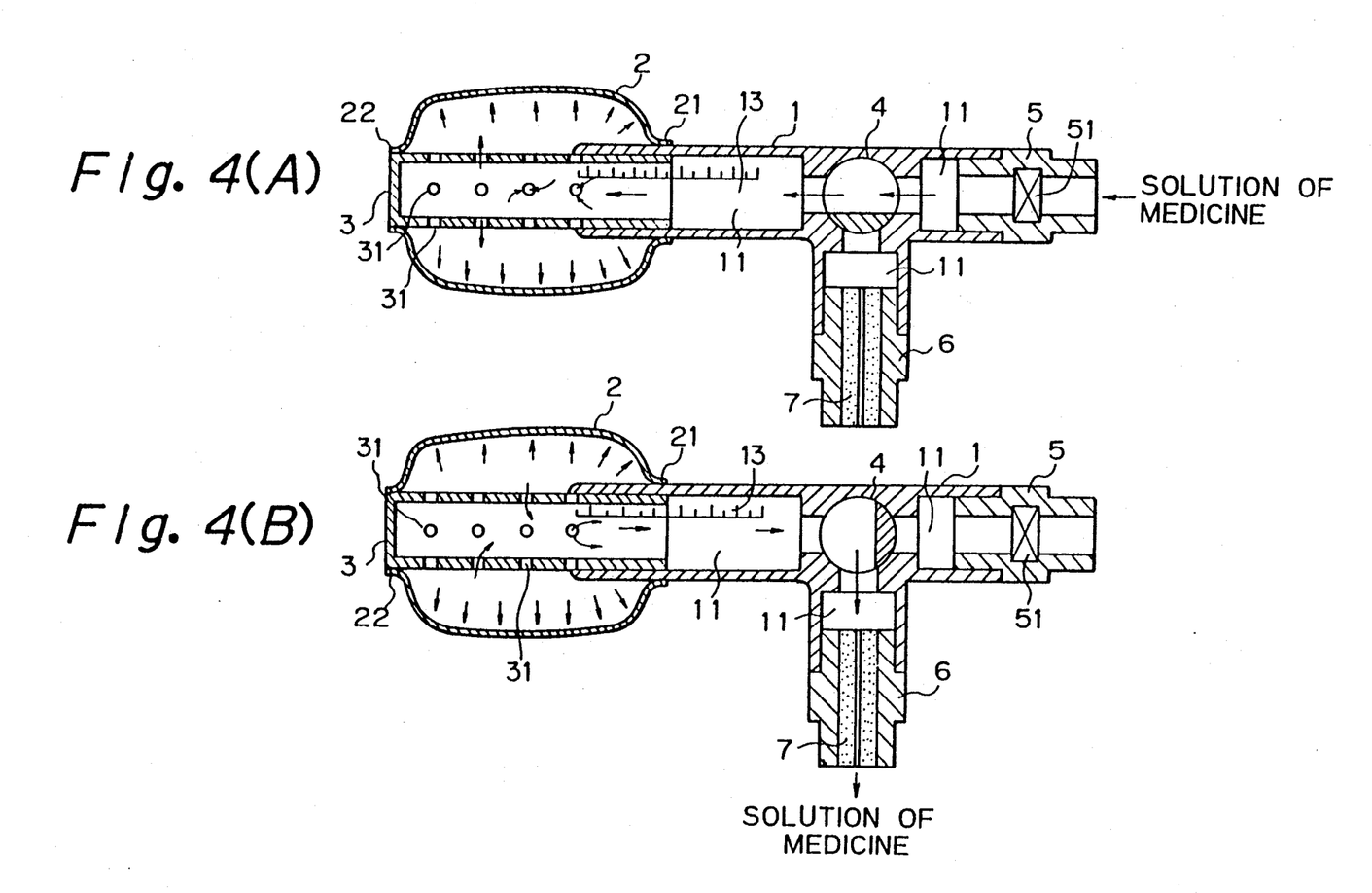
FIGS. 4(A) and 4(B) are longitudinal cross-sectional views of the infuser illustrating the operation thereof according to the present invention.

As shown in FIG. 1, the balloon 2 is tightly in contact with the tubular main body 1 and the cylinder 3 over the whole portion thereof in a normal state in which the infusion of the solution of medicine has not yet been started, while, as shown in FIG. 4, when the solution of medicine is infused into the tubular main body 1 and the cylinder 3, the balloon starts to separate from the outer periphery of the tubular main body 1 and the cylinder 3 and expands with the circumferential portions 21 and 22 thereof being left secured to the tubular main body 1 and the cylinder 3.

The control portion 7 for controlling the outflow of the solution of medicine is provided in the outlet portion 6 so that the control portion 7 communicates with the flow path 11. The control portion 7 controls an outflow time in which the solution of medicine infused in the balloon 2 flows out of the outlet portion 6.

It is desirable that the control portion 7 be selected from one of those disclosed in PCT-JP-89-00515 of the present applicant. Various modifications of this control portion 7 are shown in FIGS. 7(A)-7(F). FIGS. 7(A) to (E) show examples of the control portion 7 wherein a capillary tube 71 having a capillary hole and made from resin, metal, ceramic or the like is embedded in a synthetic resin 72. The tube 71 may be embedded in the synthetic resin 72 in a linear (A), winding (B) or spiral (C) fashion. A hole may be formed through the synthetic resin 72 by means of laser or the like in order to replace the linear capillary tube 71.

Figure 7A:
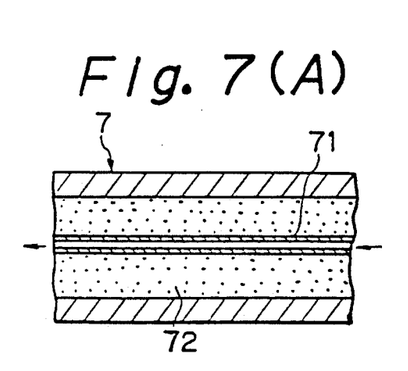
FIGS. 7(A)–7(C) are enlarged longitudinal cross-sectional views of portions of various control portions that are adapted to control the outflow of the solution of medicine from the infuser according to the present invention.
Figure 7B:
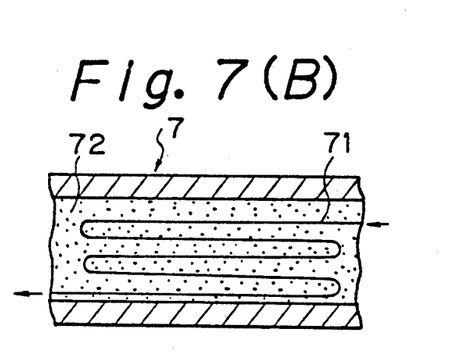
Figure 7C:
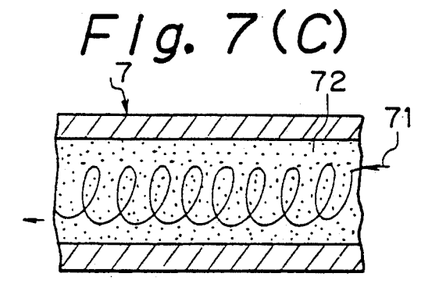
Figure 7D:
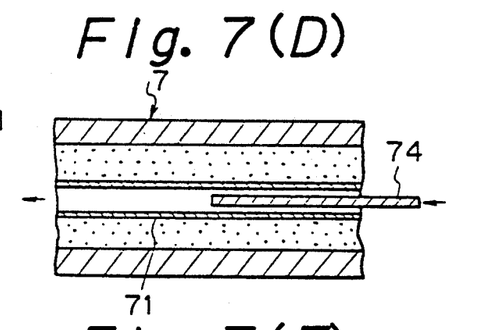
Figure 7E:
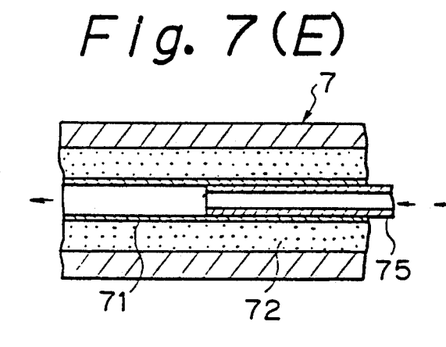

FIG. 7(D) shows an example wherein a capillary wire 74 is inserted into the capillary tube 71 in such a manner as to be allowed to move freely in and out thereof, and FIG. 7(E) shows an example wherein a tube 75 having a diameter smaller than that of the tube 71 is inserted into the latter.

Figure 7F:
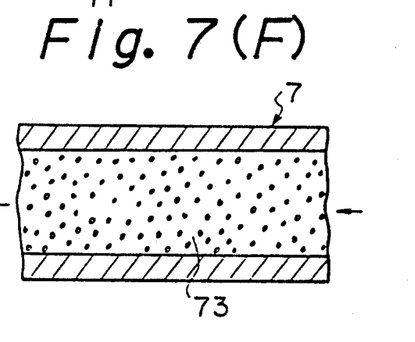

FIG. 7(F) shows an example wherein a porous material 73 fills the control portion 7. Active carbon, pumice stone, resin particles, silicone gel, urethane gel and so forth may be used as a porous or permeable and diffusible material.

The length of the capillary hole of the tube 71 or porosity of the porous or permeable and diffusible material 73 are important factors in establishing time during which the solution of medicine is allowed to flow out.

Referring to FIGS. 1 and 4, an example of the use of the infuser for continuously infusing the solution of medicine according to the present invention will now be described.

First, the inlet portion 5 is caused to be in communication with the cylinder 3 and to be shut off from the outlet 6 by the change-over valve 4 (FIG. 1).

A predetermined volume of a solution of medicine is infused into the infuser from the inlet portion 5 of the infuser. The solution of medicine is caused to flow into the balloon 2 via both the flow path 11 and holes 31 formed in the tubular main body 1, thereby causing the balloon 2 to expand. The medicine continues to be infused until the balloon becomes full. The medicine so infused into the balloon 2 is prevented from flowing in the reverse direction by means of the check valve, injection port or one-way cock 51.

In a case where the ingress of air into the balloon 2 or the flow path 11 needs to be prevented, a solution of medicine of the same type or isotonic sodium chloride solution may be infused into the flow path 11 in advance. Alternatively, the infuser is oriented to locate the inlet portion 5 at the top thereof. This allows air in the balloon 2 to enter the flow path 11 via the holes 31, and the air in the flow path 11 eventually gathers in the vicinity of the inlet portion 5. Air so gathering in the neighborhood of the inlet portion 5 can be easily discharged by means of an air bleeding capillary tube (not shown).

Figure 6A:
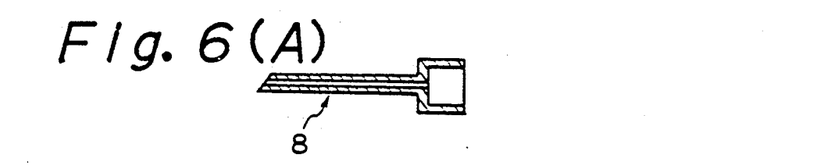
FIGS. 6(A)–6(C) are sectional views of indwelling retainers, respectively, for the human body which are designed to be connected to the infuser for continuously infusing the solution of medicine according to the present invention.
Figure 6B:
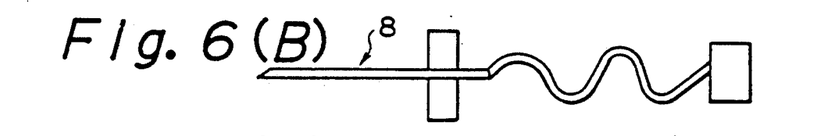
Figure 6C:
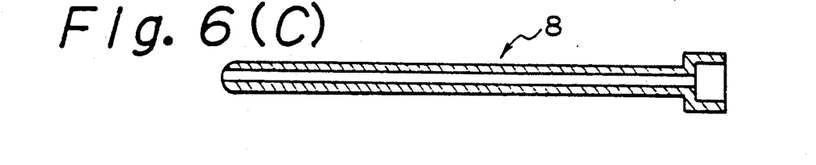

After a predetermined volume of the medicine has been infused into the balloon 2, a cap (not shown) attached to the distal end of the outlet portion 6 is then taken off, and a separately prepared indwelling retainer 8 for the human body, such as an injecting needle, is fitted to the outlet portion 6 (FIG. 6).

Next, the cylinder 3 is placed in communication with the outlet portion 6 by operating the change-over valve 4 (FIG. 5(B)). Then, the inlet portion 4 may either communicate with the outlet portion 6 or be shut off from the outlet portion 6. Even if the inlet portion 5 communicates with the outlet portion 6, the one-way cock 51 prevents the solution of medicine from flowing out of the inlet portion 5.

The medicine filling the balloon 2 is caused to flow into the injecting needle or the like via the holes 31, the flow path 11, the capillary tube 71 having a capillary hole, and the outlet portion 6 by virtue of the contracting action of the balloon 2.

Finally, a normal air bleeding operation is carried out. In order to confirm whether air has been completely bled, the respective constituent elements should desirably be transparent or translucent.

The injecting time of the solution of medicine depends on the volume of the medicine infused in the balloon 2 and the viscosity of the medicine, the contraction properties of the balloon 2, the transverse cross-sectional area and length of the capillary hole, the internal pressure of a part of the human body where the medicine is infused, and so forth. The actual injecting time of the infuser may be measured by employing a standard solution of medicine, and this may be carried out on each infuser.

When the balloon expands and contracts, the cylinder 3 moves relative to the tubular main body owing to the elasticity of the balloon 2 and the pressure of the solution of medicine in the balloon 2. This movement of the cylinder 3 makes the expansion and contraction of the balloon 2 uniform, since the balloon 2 is expanded or contracted by the same value in the longitudinal axial direction and in the axial direction perpendicular to the longitudinal axial direction.

Figure 8:
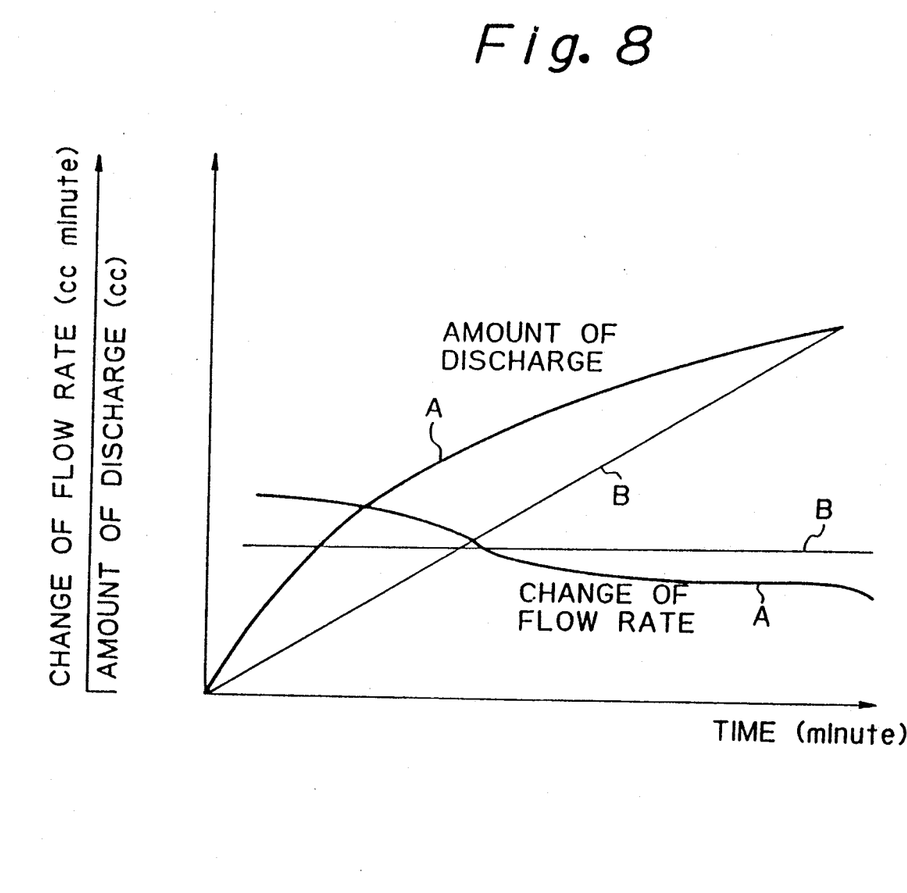
FIG. 8 is a graph of flow characteristics of the infuser according to the present invention and according to the prior art.

Consequently, as shown in FIG. 8, outflow characteristics B of the infuser according to the present invention are always uniform in comparison with outflow characteristics A of the infuser according to the prior art (PCT-JP-89-00515).

FIGS. 6(A)–(C) shows main examples of indwelling retainers 8 for the human body that may be connected to the outlet portion 6 of the infuser of the present invention. FIG. 6(A) shows a normal injecting needle, FIG. 6(B) an injecting needle having a flexible conduit, and FIG. 6(C) a normal catheter.

Basically, a spherical balloon 2 is employed in the present invention, but the balloon 2 used may be of any shape depending on the infusing site of the human body. For instance, a flat elliptical balloon may be utilized.

Figure 9A:
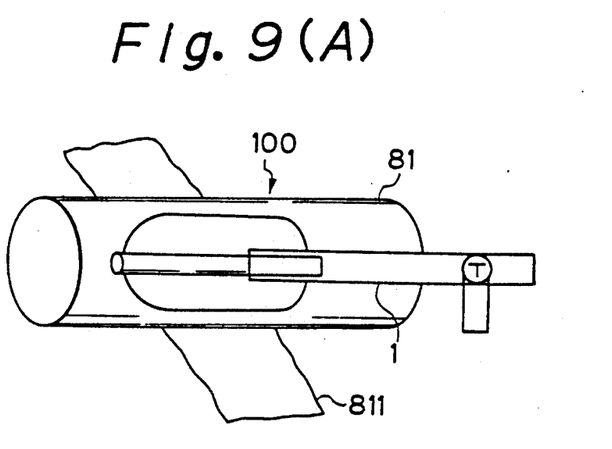
FIGS. 9(A)-9(F) are schematic diagrams of various applications of the infuser for continuously infusing the solution of medicine according to the present invention.
Figure 9B:
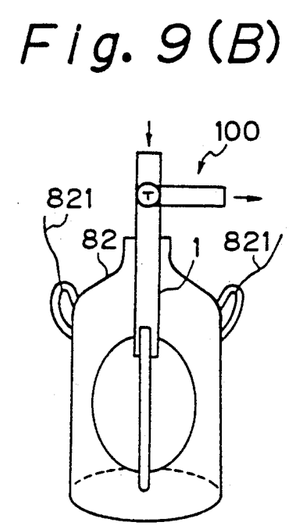

A transparent cover 81 [FIGS. 9(A) or (B)] covering the exterior of the balloon 2 may be detachably mounted on the tubular main body 1 to prevent the balloon from being ruptured by contact with an article having a sharp point, edge or the like. In this case, a belt 811 or a strap 821 is preferably provided so as to facilitate the securing of the infuser 100 to the human body.

Figure 9C:
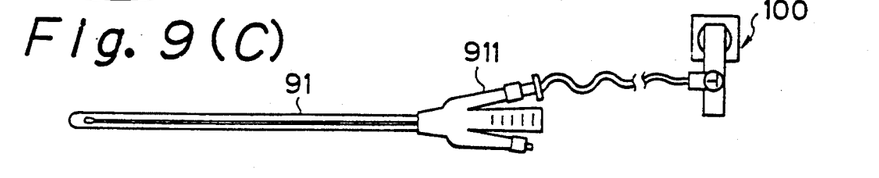

FIG. 9(C) shows an example wherein the infuser 100 for continuously infusing a solution of medicine according to the present invention is connected to the inlet portion 911 of a catheter 91 for the urinary or digestive organs.

Figure 9D:
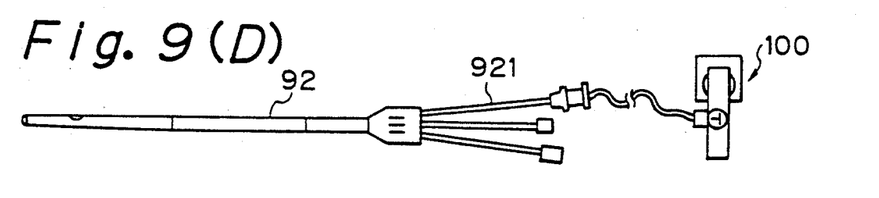

FIG. 9(D) shows an example wherein the infuser 100 for continuously infusing a solution of medicine according to the present invention is connected to the inlet portion 921 of a catheter 92 for veins.

Figure 9E:
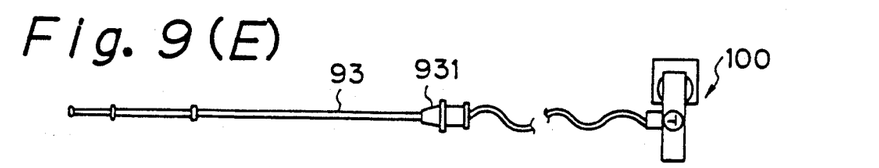

FIG. 9(E) shows an example wherein the infuser 100 for continuously infusing a solution of medicine according to the present invention is connected to the inlet portion 931 of a catheter 93 for use in the field of obstetrics and gynecology.

Figure 9F:
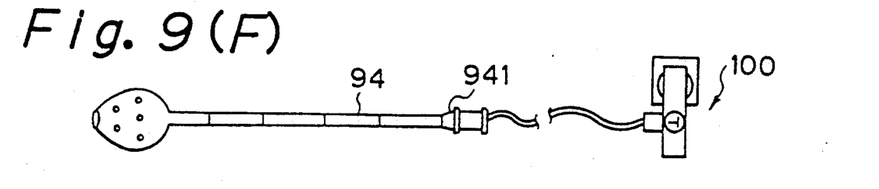

FIG. 9(F) shows an example wherein the infuser 100 for continuously infusing a solution of medicine according to the present invention is connected to the inlet portion 941 of a catheter 94 for use in the field of encephalon surgery.

Since the infuser for continuously infusing a solution of medicine in accordance with the present invention is adapted to function not only as a container for a medicine but also as a drug infuser, it has a simple structure and is easy to handle. The infuser of the present invention does not restrict the action and movement of the patient, and reduces the labour and actual working hours of the operator. Moreover, once air is bled, the ingress of air is not allowed until the balloon is completely contracted.

Furthermore, the infuser in accordance with the present invention has uniform outflow characteristics for the solution of medicine.

I claim:

1. An infuser for continuously infusing a solution of medicine, comprising:

a tubular main body defining a flow path therein which extends along the longitudinal axis of said body;

an inlet portion integral with one end of said body, said inlet portion having one-way flow means for allowing a solution to flow in one direction into the infuser and toward said flow path from the inlet portion;

a cylinder having a closed bottom, said cylinder being slidably connected to the other end of said body with the bottom of said cylinder being directed outwardly thereof, said cylinder or the other end of said body having a plurality of holes extending therethrough;

a change-over valve disposed in said flow path at an intermediate portion of said tubular main body;

an outlet portion communicating with said flow path via said change-over valve so as to allow a solution of medicine to be discharged from the infuser;

a control element disposed in said outlet portion and adapted to control the flow of a solution of medicine out of the infuser through said outlet portion;

a balloon of an elastic material encompassing said holes, said balloon having one circumferential portion air-tightly secured to the outer periphery of said body at a first position thereon and another circumferential portion air-tightly secured to the outer periphery of said cylinder at a second position thereon; and said change-over valve being moveable between at least a first position at which said flow path is open between the ends of said tubular main body while said outlet portion is closed to the flow path by said valve whereby a solution of medicine can be introduced into the infuser without flowing out of said outlet portion and a second position at which said flow path is open between said other end of said tubular main body and said outlet portion whereby a solution of medicine in the infuser can flow from said outlet portion through said control member.

2. An infuser as set forth in claim 1, wherein said main tubular body has scale marks spaced longitudinally on an outer peripheral portion thereof which slidingly supports the cylinder.

* * * * *